United States Patent
Hsu

(10) Patent No.: US 10,695,209 B2
(45) Date of Patent: Jun. 30, 2020

(54) SCOLIOSIS ACTIVITY SUIT

(71) Applicant: Wen Hua Hsu, Kaohsiung (TW)

(72) Inventor: Wen Hua Hsu, Kaohsiung (TW)

( * ) Notice: Subject to any disclaimer, the term of this patent is extended or adjusted under 35 U.S.C. 154(b) by 375 days.

(21) Appl. No.: 15/784,071

(22) Filed: Oct. 13, 2017

(65) Prior Publication Data

US 2018/0140454 A1  May 24, 2018

(30) Foreign Application Priority Data

Nov. 22, 2016 (TW) .............................. 105138212 A

(51) Int. Cl.
*A61F 5/37* (2006.01)
*A61F 5/02* (2006.01)
(Continued)

(52) U.S. Cl.
CPC ............... *A61F 5/024* (2013.01); *A61F 5/02* (2013.01); *A61F 5/026* (2013.01); *A61H 1/008* (2013.01); *A61F 2005/0197* (2013.01)

(58) Field of Classification Search
CPC .. A61F 5/02; A61F 5/024; A61F 5/026; A61F 5/028; A61F 5/37;
(Continued)

(56) References Cited

U.S. PATENT DOCUMENTS 5,599,286 A    2/1997 Labelle et al.
5,628,725 A *  5/1997 Ostergard ............. A61F 5/3746
                                                      602/20
(Continued)

FOREIGN PATENT DOCUMENTS

JP    2008-279065 A    11/2008
JP    2010-261118 A    11/2010
(Continued)

OTHER PUBLICATIONS

English language Abstract of JP 2008-279065 A (Nov. 20, 2008).
(Continued)

*Primary Examiner* — Anna K Kinsaul
*Assistant Examiner* — Camtu T Nguyen
(74) *Attorney, Agent, or Firm* — Hershkovitz & Associates, PLLC; Abe Hershkovitz

(57) ABSTRACT

A scoliosis activity suit includes a body-wrapping portion and a correction portion. The correction portion has a front segment, a rear segment, a shoulder-pulling segment, a chest-pressing segment, a pelvis-lifting segment, and a upper trapezius pressing segment. The shoulder-pulling segment, the chest-pressing segment, the pelvis-lifting segment, and the upper trapezius pressing segment are formed on a front side of the body-wrapping portion and extend to the rear segment of the correction portion. To users with scoliosis, the correction portion generates a 3D compression force on different portions of the spine of the user, such that a backward pulling force against a protracted portion of the shoulder, an uplifting force against an inclined portion of the pelvis, and a pulling force against portions with spinal sidebend can be provided. Besides, being lightweight and easy for users to wear, the suit fulfills practice of daily life adjustment and correction for scoliosis.

7 Claims, 12 Drawing Sheets

(51) Int. Cl.
*A61H 1/00* (2006.01)
*A61F 5/01* (2006.01)

(58) Field of Classification Search
CPC ... A61F 2005/0197; A61H 1/008; A41D 1/04;
A41D 13/00; A41D 13/02; A41D
2300/22; A41C 1/00; A41C 1/06; A41C
1/08; A41C 1/10; A41C 3/0057; A63B
21/0552
See application file for complete search history.

(56) References Cited

U.S. PATENT DOCUMENTS

| | | | | |
|---|---|---|---|---|
| 7,374,523 | B2* | 5/2008 | Weir | A63B 21/0004 482/148 |
| 8,007,457 | B2* | 8/2011 | Taylor | A61F 5/0102 2/69 |
| 8,795,213 | B2 | 8/2014 | Mills | |
| 9,168,167 | B2* | 10/2015 | Brown | A61F 5/026 |
| 2008/0208089 | A1* | 8/2008 | Newkirk | A61F 5/026 602/19 |
| 2010/0217166 | A1 | 8/2010 | Mills | |
| 2014/0174454 | A1 | 6/2014 | Naef | |
| 2014/0296759 | A1 | 10/2014 | Matthews | |
| 2015/0313295 | A1* | 11/2015 | Bye | A41D 13/02 2/456 |

FOREIGN PATENT DOCUMENTS

| | | |
|---|---|---|
| JP | 5879919 B2 | 3/2016 |
| WO | WO 2013/030610 A1 | 3/2013 |

OTHER PUBLICATIONS

English language Abstract of JP 2010-261118 A (Nov. 18, 2010).
English language Abstract of JP 5879919 B2 (Mar. 8, 2016).
Extended European Search Report dated Apr. 11, 2018 in counterpart Application No. EP 17 20 1303.9.
Search Report dated Jun. 12, 2017 in counterpart Application No. TW 105138212.

* cited by examiner

SCOLIOSIS ACTIVITY SUIT

BACKGROUND OF THE INVENTION

1. Field of the Invention

The present invention relates to a scoliosis activity suit and, more particularly, to a scoliosis activity suit that is light in weight and can be comfortably and conveniently worn on a user during daily life.

2. Description of the Related Art

Spine is a crucial structure supporting and giving the form of a human body and is upright in a normal condition when viewed from the back of the body. In most cases of curved sidebend and vertebral rotation, the spine may have one to three curved segments along with axial rotation. Such sidebend may be C-shaped or S-shaped and is usually called scoliosis. The majority of scoliosis cases originate from congenital abnormalities and modern medicine has not yet come to a conclusion about the causes of scoliosis so far. Some believe that acquired scoliosis may result from back muscle weakness caused by bad posture and a lack of muscle training. No matter how scoliosis is caused, the resultant curved sidebend affects human physical appearance eventually. Perhaps because of uneven shoulders, shoulder protraction or spinal curvature toward the left chest or right chest, also lumbar sidebend, and pelvic torsion, bodies with those abnormalities are prone to back pain, sore waist, muscle weakness and/or aggravated spinal sidebend. Serious cases of scoliosis arising from weakness in the spine can further cause compression on the spinal cord or internal organs. As a result, scoliosis should be corrected as early as possible to prevent spinal sidebend from deteriorating.

However, conventional scoliosis correction equipment is hard to be carried along and may be unconformtably or inconveniently worn during daily life. Even though the spinal sidebend can be temporarily corrected when the scoliosis correction equipment is applied, the spinal sidebend comes back again after the scoliosis correction equipment is removed. Sustaining the practice of daily life adjustment and correction for scoliosis becomes an issue bothering people with scoliosis.

SUMMARY OF THE INVENTION

An objective of the present invention is to provide a scoliosis activity suit being lightweight and convenient for users to wear for fulfilling practice of daily life adjustment and correction for scoliosis.

To achieve the foregoing objective, the scoliosis activity suit includes a body-wrapping portion and a correction portion.

The body-wrapping portion is made of elastic fabric.

The correction portion is made of elastic fabric, is formed on the body-wrapping portion, and has a front segment, a rear segment, a shoulder-pulling segment, a chest-pressing segment, a pelvis-lifting segment, and an upper trapezius-pressing segment. The front segment is formed on a front side of the body-wrapping portion.

The rear segment is formed on a rear side of the body-wrapping portion.

The shoulder-pulling segment is formed on the front side of the body-wrapping portion, extends to the rear segment, and is disconnected from the front segment.

The chest-pressing segment is formed on the front side of the body-wrapping portion, is connected with the front segment, and extends laterally from the front segment to the rear segment.

The pelvis-lifting segment is formed on the front side of the body-wrapping portion, is connected with the front segment, and extends laterally from the front segment to the rear segment.

The upper trapezius pressing segment is formed on the front side of the body-wrapping portion, is connected with the front segment, and extends from the front segment to the rear segment. The chest-pressing segment is located between the shoulder-pulling segment and the pelvis-lifting segment.

Preferably, the body-wrapping portion has a zipper, a first side edge, a second side edge, a first shoulder line and a second shoulder line. The zipper is mounted on the front side of the body-wrapping portion. The first side edge is formed on a first lateral edge of the body-wrapping portion. The second side edge is formed on a second lateral edge of the body-wrapping portion and is opposite to the first side edge. The first shoulder line is formed on the body-wrapping portion and is located above the first side edge. The second shoulder line is formed on the body-wrapping portion, is located above the second side edge, and is spaced apart from the first shoulder line.

According to the foregoing description, after put on by a user with scoliosis, the scoliosis activity suit applies a 3D compression force to correct the alignment of shoulder girdle, chest, rib cage and pelvis of the body to generate a backward pulling force against a protracted portion of the shoulder, an uplifting force against an inclined portion of the pelvis, and a pulling force against a portion with spinal sidebend. The scoliosis activity suit is lightweight and can be comfortably and conveniently worn on the user to fulfill practice of daily life adjustment and correction for scoliosis.

Other objectives, advantages and novel features of the invention will become more apparent from the following detailed description when taken in conjunction with the accompanying drawings.

DETAILED DESCRIPTION OF THE INVENTION

Figure 1:
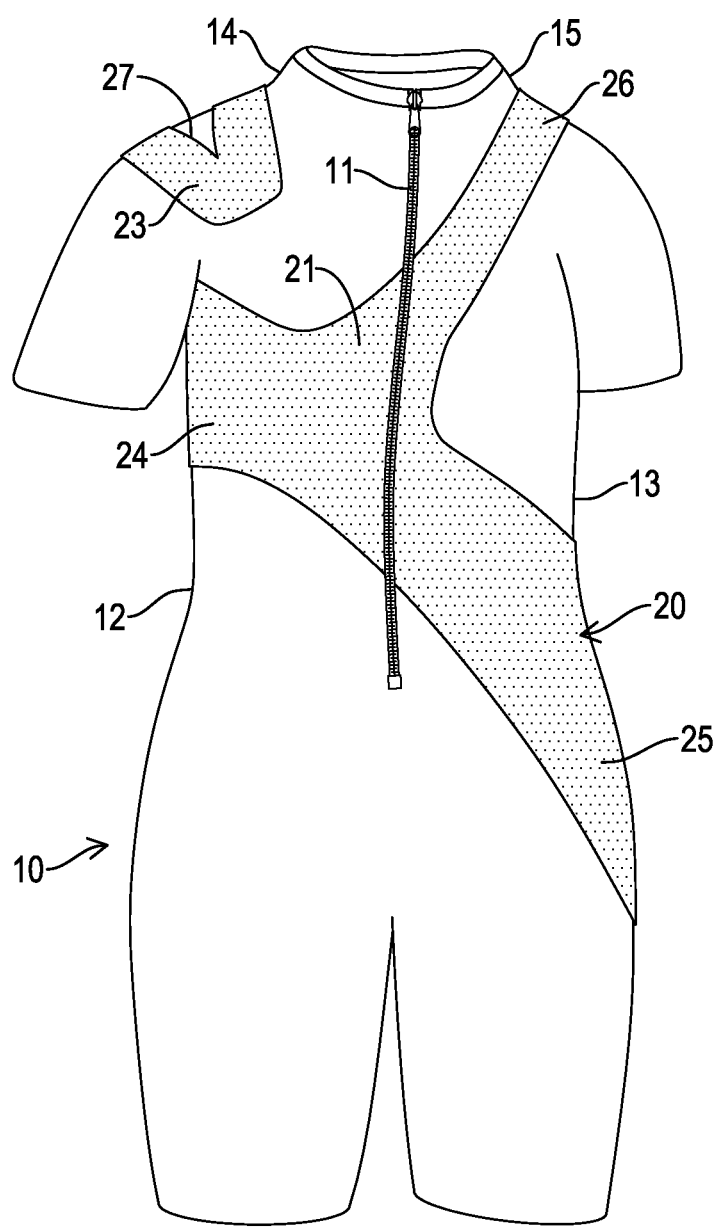
FIG. 1 is a schematic front view of a first embodiment of a scoliosis activity suit in accordance with the present invention.

With reference to FIGS. 1, 4, 7 and 10, several embodiments of a scoliosis activity suit in accordance with the present invention are illustrated and each embodiment of the scoliosis activity suit includes a body-wrapping portion 10 and a correction portion 20. The body-wrapping portion 10 is a common portion to all the embodiments in the present invention.

The body-wrapping portion 10 is made of elastic fabric and has a zipper 11, a first side edge 12, a second side edge 13, a first shoulder line 14 and a second shoulder line 15. The zipper 11 is mounted on a front side of the body-wrapping portion 10. The first side edge 12 is formed on a first lateral edge of the body-wrapping portion 10. The second side edge 13 is formed on a second lateral edge of the body-wrapping portion 10 and is opposite to the first side edge 12. In the present embodiment, the first side edge 12 and the second side edge 13 are located at a right edge and a left edge of the body-wrapping portion 10. The first shoulder line 14 is formed on the body-wrapping portion 10 and is located above the first side edge 12. The second shoulder line 15 is formed on the body-wrapping portion 10, is located above the second side edge 13, and is spaced apart from the first shoulder line 14.

Figure 2:
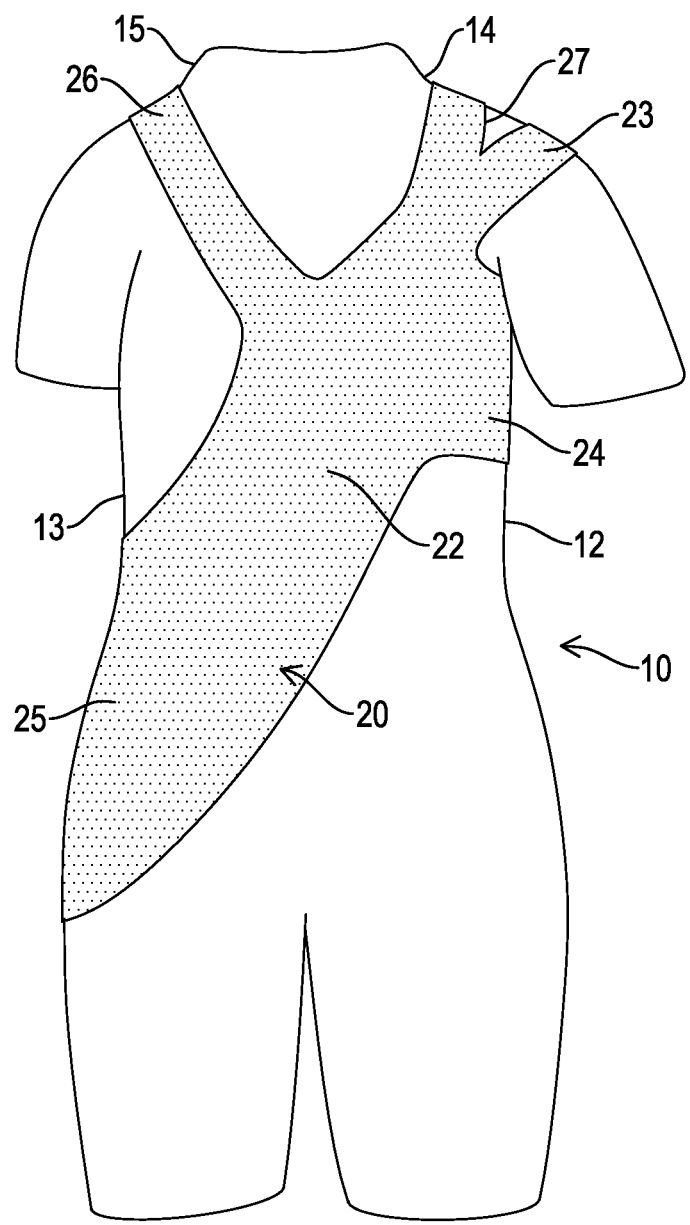
FIG. 2 is a schematic rear view of the scoliosis activity suit in FIG. 1.

With reference to FIGS. 1 and 2, a first embodiment of a scoliosis activity suit in accordance with the present invention is shown. The correction portion 20 of the scoliosis activity suit is made of elastic fabric, is formed on the body-wrapping portion 10, and has a front segment 21, a rear segment 22, a shoulder-pulling segment 23, a chest-pressing segment 24, a pelvis-lifting segment 25, and an upper trapezius pressing segment 26. The front segment 21 is formed on the front side of the body-wrapping portion 10. The rear segment 22 is formed on a rear side of the body-wrapping portion 10. The shoulder-pulling segment 23 is formed on the front side of the body-wrapping portion 10, extends from the front side of the body-wrapping portion 10 to the rear segment 22 through the first shoulder line 14, is disconnected from the front segment 21, and has a stretchable opening 27 formed through the shoulder-pulling segment 23. The chest-pressing segment 24 is formed on the front side of the body-wrapping portion 10, is connected with the front segment 21, extends laterally from the front segment 21 to the rear segment 22 through the first side edge 12, and is located between the shoulder-pulling segment 23 and the pelvis-lifting segment 25. The pelvis-lifting segment 25 is formed on the front side of the body-wrapping portion 10, is connected with the front segment 21, and extends laterally from the front segment 21 to the rear segment 22 through the second side edge 13. The upper trapezius pressing segment 26 is formed on the front side of the body-wrapping portion 10, is connected with the front segment 21, and extends from the front segment 21 to the rear segment 22 through the second shoulder line 15.

Figure 4:
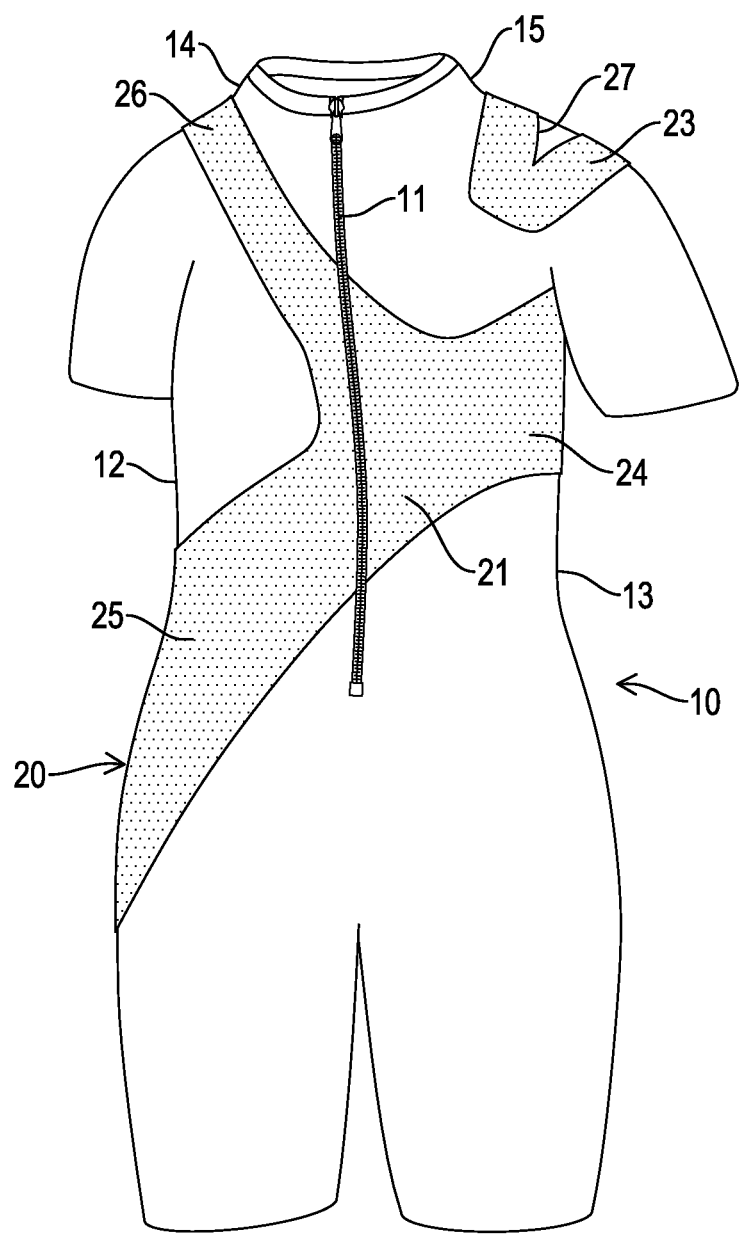
FIG. 4 is a schematic front view of a second embodiment of a scoliosis activity suit in accordance with the present invention.
Figure 5:
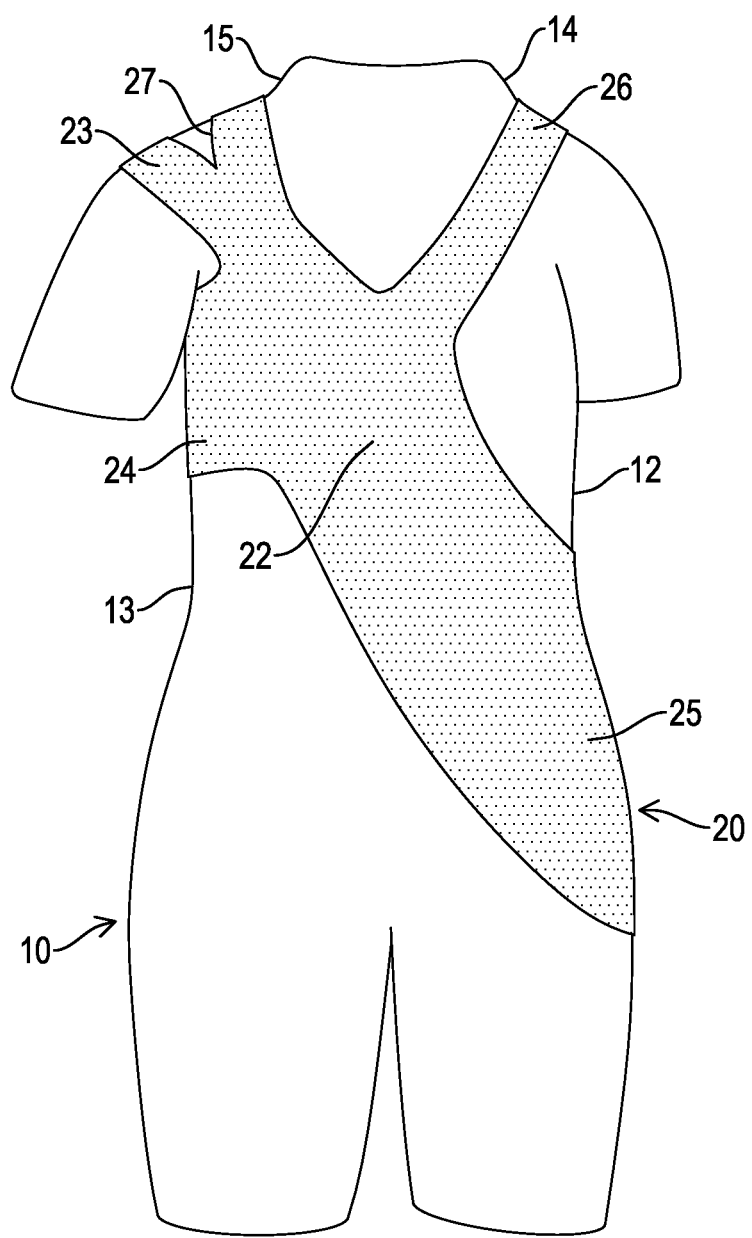
FIG. 5 is a schematic rear view of the scoliosis activity suit in FIG. 4.

With reference to FIGS. 4 and 5, a second embodiment of a scoliosis activity suit in accordance with the present invention differs from the first embodiment in the layout of the shoulder-pulling segment 23, the chest-pressing segment 24, the pelvis-lifting segment 25 and the upper trapezius pressing segment 26. The shoulder-pulling segment 23 is formed on the front side of the body-wrapping portion 10, is connected with the front segment 21, and extends from the front segment to the rear segment 22 through the second shoulder line 15. The chest-pressing segment 24 is formed on the front side of the body-wrapping portion 10, is connected with the front segment 21, and extends laterally from the front segment 21 to the rear segment 22 through the first side edge 12. The upper trapezius pressing segment 26 is formed on the front side of the body-wrapping portion 10, is connected with the front segment 21, and extends from the front segment 21 to the rear segment 22 through the first shoulder line 14.

Figure 7:
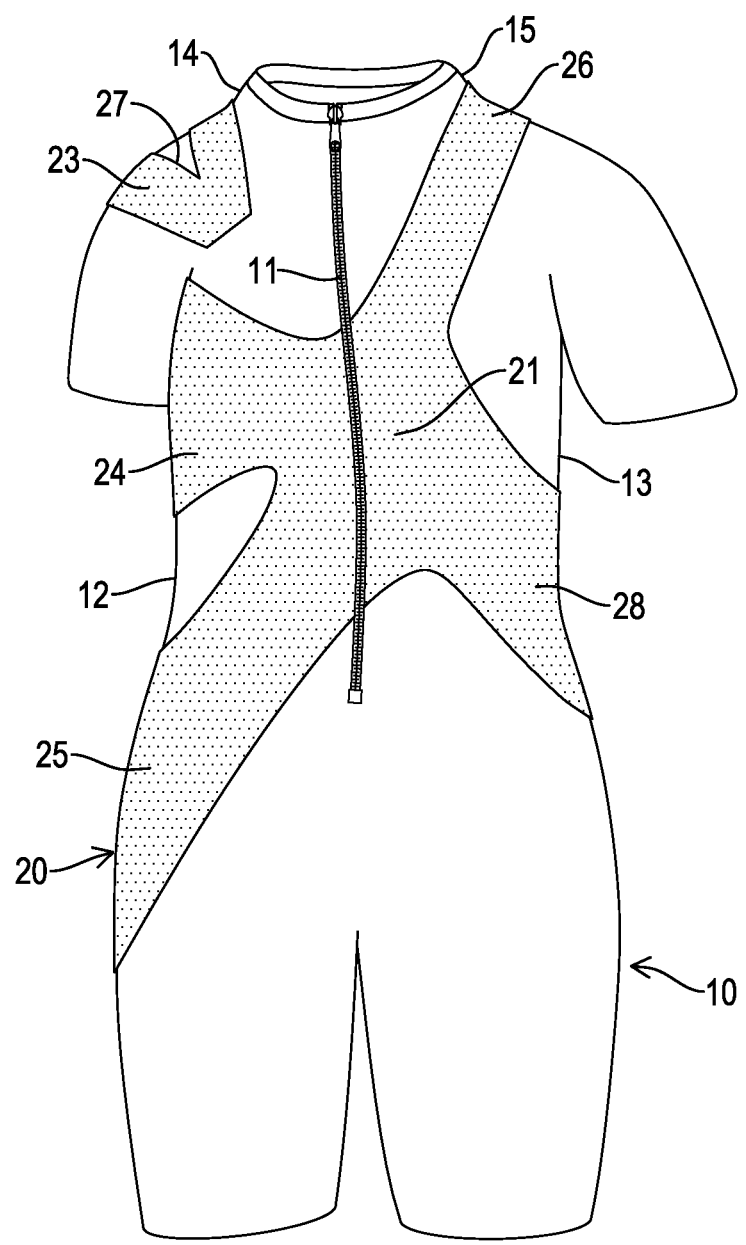
FIG. 7 is a schematic front view of a third embodiment of a scoliosis activity suit in accordance with the present invention.
Figure 8:
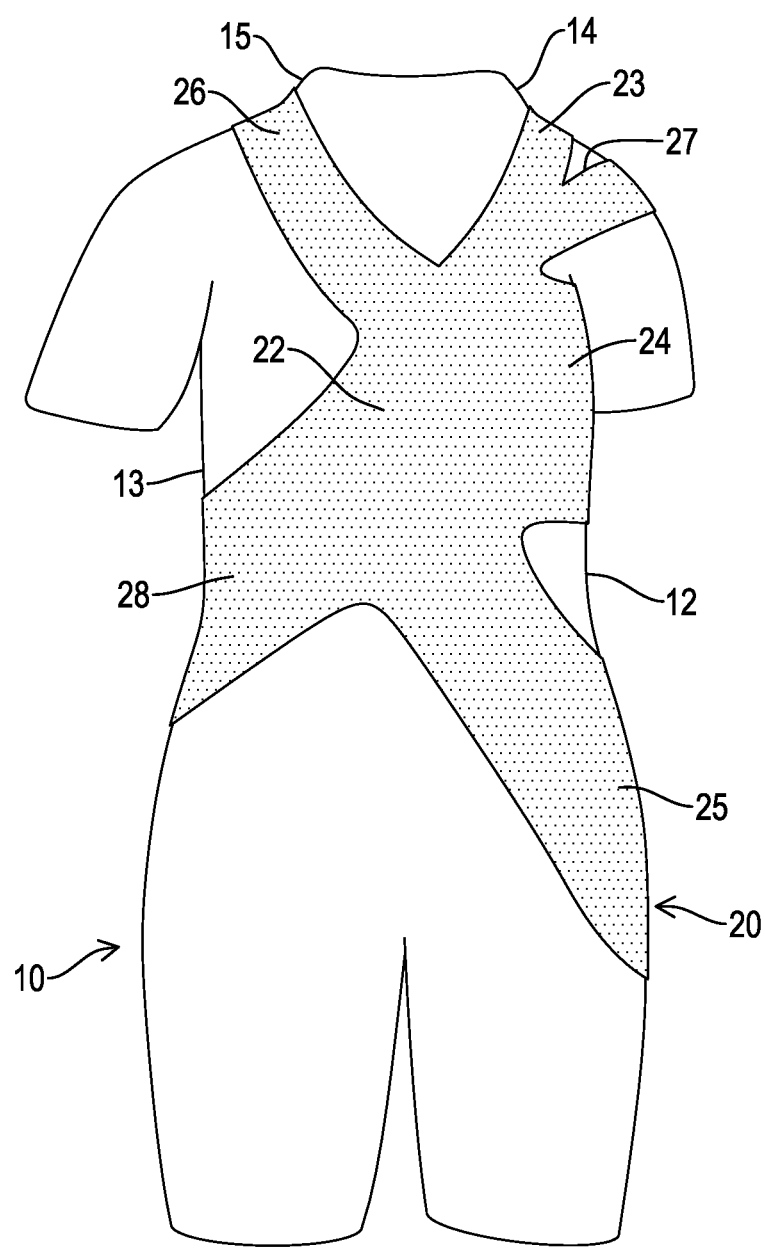
FIG. 8 is a schematic rear view of the scoliosis activity suit in FIG. 7.

With reference to FIGS. 7 and 8, a third embodiment of a scoliosis activity suit in accordance with the present invention differs from the first embodiment in the layout of the pelvis-lifting segment 25 and an additional waist-pressing segment 28. The pelvis-lifting segment 25 is formed on the front side of the body-wrapping portion 10, is connected with the front segment 21, and extends from the front segment 21 to the rear segment 22 through the first side edge 12. The waist-pressing segment 28 is formed on the front side of the body-wrapping portion 10, is connected with the front segment 21, extends laterally from the front segment 21 to the rear segment 22 through the second side edge 13, and is located between the chest-pressing segment 24 and the pelvis-lifting segment 25.

Figure 10:
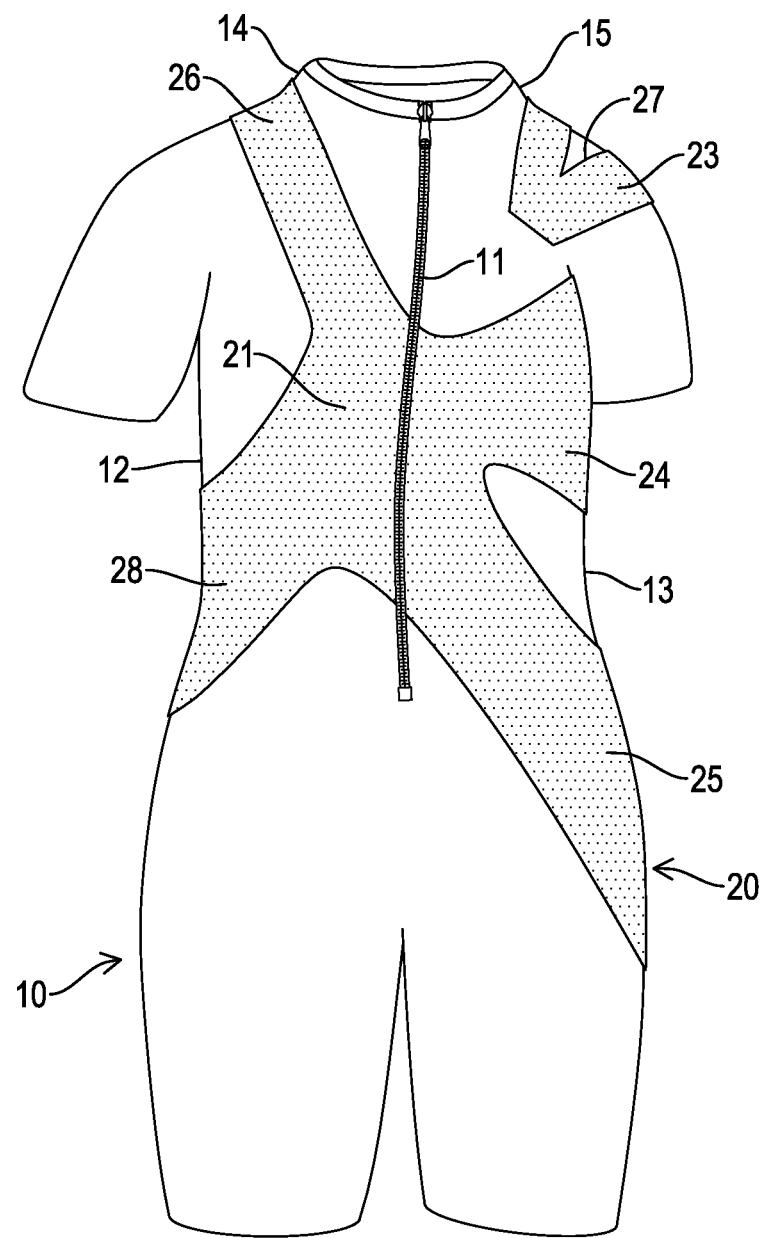
FIG. 10 is a schematic front view of a fourth embodiment of a scoliosis activity suit in accordance with the present invention.
Figure 11:
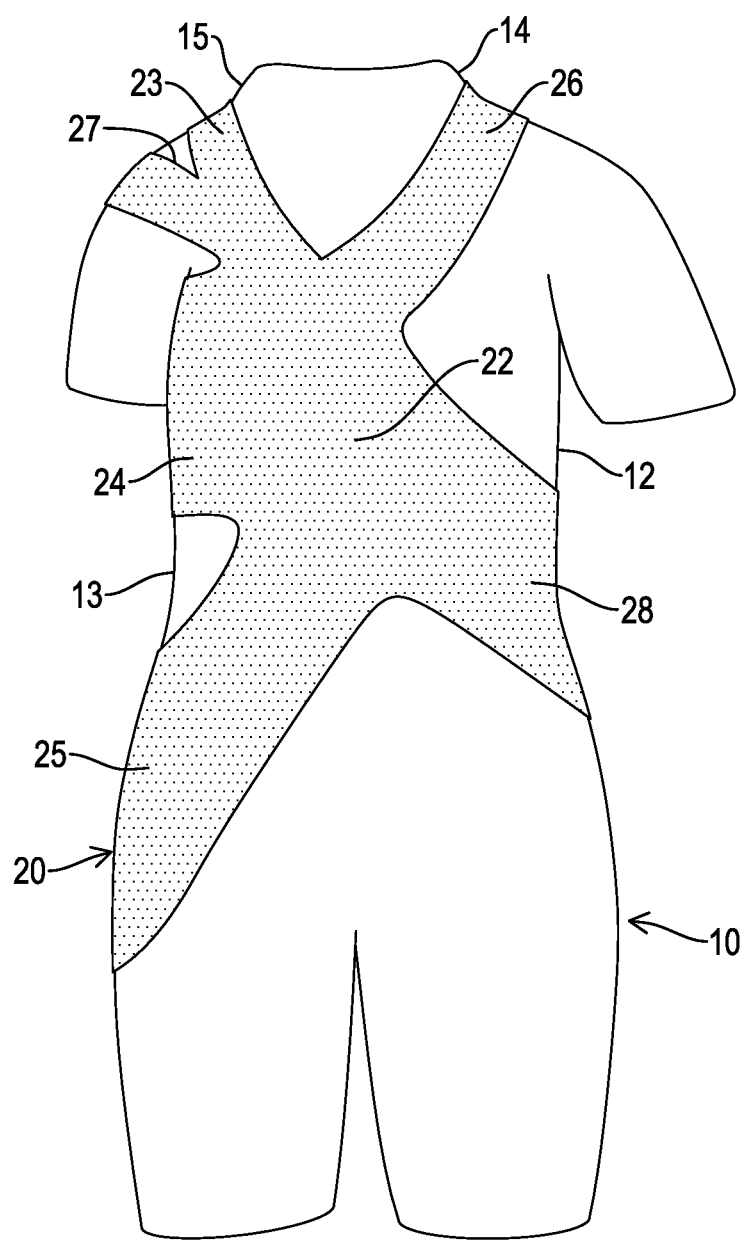
FIG. 11 is a schematic rear view of the scoliosis activity suit in FIG. 10.

With reference to FIGS. 10 and 11, a fourth embodiment of a scoliosis activity suit in accordance with the present invention differs from the second embodiment in the layout of the pelvis-lifting segment 25 and an additional waist-pressing segment 28. The pelvis-lifting segment 25 is formed on the front side of the body-wrapping portion 10, is connected with the front segment 21, and extends from the front segment 21 to the rear segment 22 through the second side edge 13. The waist-pressing segment 28 is formed on the front side of the body-wrapping portion 10, is connected with the front segment 21, extends laterally from the front segment 21 to the rear segment 22 through the first side edge 12, and is located between the chest-pressing segment 24 and the pelvis-lifting segment 25.

With reference to FIGS. 3, 6, 9 and 12, the foregoing embodiments of the scoliosis activity suit are worn on users with different forms of sidebend of the spine 30 as indicated by corresponding force-exerted regions 40 for scoliosis correction. The force-exerted region 40 shown in each of FIGS. 3 and 6 corresponds to C-shaped spinal sidebend and includes a shoulder area 41, a chest area 42 and a pelvis area 44. The force-exerted region 40 shown in each of FIGS. 9 and 12 corresponds to S-shaped spinal sidebend and includes a shoulder area 41, a chest area 42, a waist area 43 and a pelvis area 44. When the scoliosis activity suit is worn on a user, the force-exerted region 40 is subject to a pressure through the correction portion 20 of the scoliosis activity suit. The portion of the spine 30 over the shoulder is pushed by a force exerted on the shoulder area 41 to protract toward a forward direction, and the shoulder-pulling segment 23 of the correction portion 20 extends from the front side of the body-wrapping portion 10 to the rear segment 22 and is disconnected from the front segment 21 to provide a backward pulling force to compensate the force toward the forward direction. The portion of the spine 30 over the chest is bent by a force exerted on the chest area 42, and the chest-pressing segment 24 of the correction portion 20 is connected with the front segment 21 and extends laterally from the front side of the body-wrapping portion 10 to the rear segment 22 to provide a pulling force opposite to the force exerted on the chest area 42 to compensate the force.

The portion of the spine 30 over the waist is bent by a force exerted on the waist area 43, and the waist-pressing segment 28 of the correction portion 20 is connected with the front segment 21 and extends laterally from the front side of the body-wrapping portion 10 to the rear segment 22 to provide a pulling force opposite to the force exerted on the waist area 43 to compensate the force. The portion of the spine 30 over the pelvis is descended by a force exerted on the pelvis area 44, and the pelvis-lifting segment 25 of the correction portion 20 is connected with the front segment 21 and extends laterally from the front side of the body-wrapping portion 10 to the rear segment 22 to provide an uplifting force to compensate the force.

Figure 3:
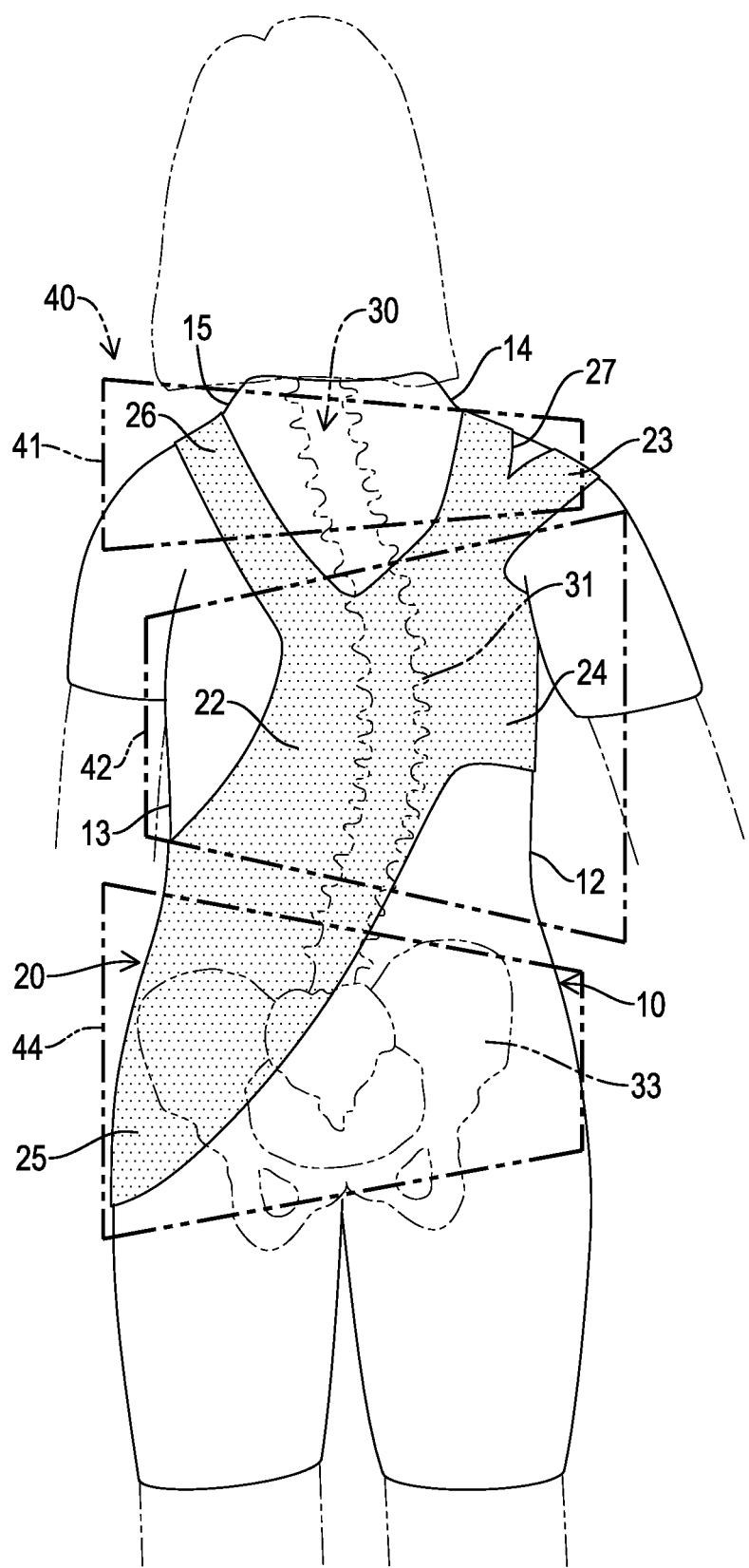
FIG. 3 is an operational schematic view of the scoliosis activity suit in FIG. 1.

With further reference to FIGS. 1 to 3, the first embodiment targets at correcting C-shaped sidebend of the spine 30, which is typically represented by a chest spine portion 31 bent toward the first side edge 12, a shoulder portion of the spine 30 over the first shoulder line 14 protracted forwards, and a pelvis 33 inclined toward the second side edge 13. When a user intends to wear the scoliosis activity suit, the zipper 11 on the front side of the body-wrapping portion 10 is unzipped for the scoliosis activity suit to be worn on the user. The shoulder-pulling segment 23 of the correction portion 20 provides a backward pulling force to the shoulder protracted forwards. The chest-pressing segment 24 provides a pulling force toward the second side edge 13 to the chest spine portion 31 bent toward the first side edge 12. The pelvis-lifting segment 25 provides an uplifting force to the pelvis 33 inclined toward the second side edge 13. The upper trapezius pressing segment 26 provides a supporting force to the portion of the spine 30 over the shoulder, the chest spine portion 31 and the pelvis 33.

Figure 6:
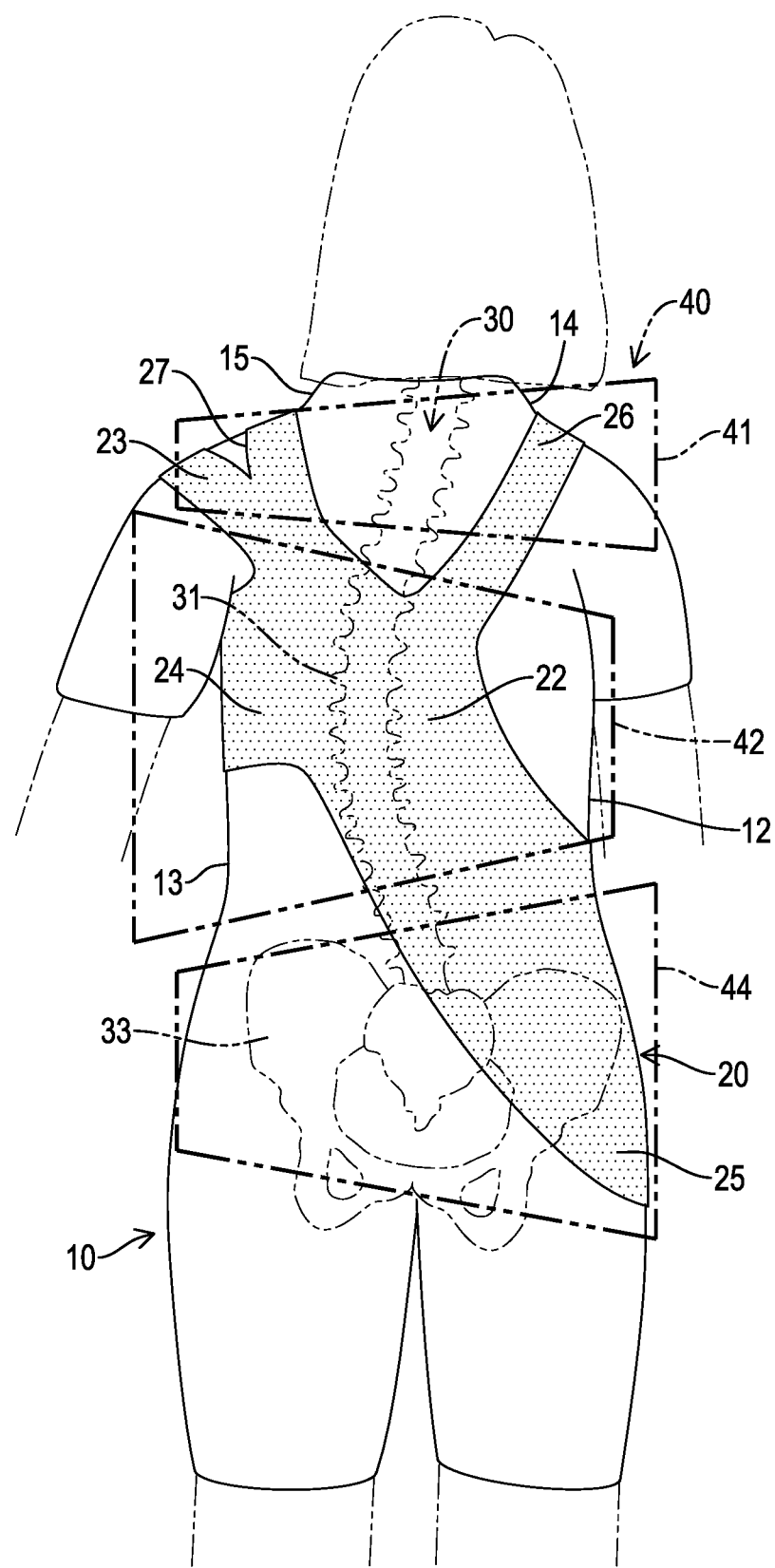
FIG. 6 is an operational schematic view of the scoliosis activity suit in FIG. 4.

With further reference to FIGS. 4 to 6, the second embodiment targets at correcting C-shaped sidebend of the spine 30, which is typically represented by the chest spine portion 31 bent toward the second side edge 13, the shoulder portion of the spine 30 over the second shoulder line 14 protracted forwards, and the pelvis 33 inclined toward the first side edge 12. When a user intends to wear the scoliosis activity suit, the zipper 11 on the front side of the body-wrapping portion 10 is unzipped for the scoliosis activity suit to be worn on the user. The shoulder-pulling segment 23 of the correction portion 20 provides a backward pulling force to the shoulder protracted forwards. The chest-pressing segment 24 provides a pulling force toward the first side edge 12 to the chest spine portion 31 bent toward the second side edge 13. The pelvis-lifting segment 25 provides an uplifting force to the pelvis 33 inclined toward the first side edge 12. The upper trapezius pressing segment 26 provides a supporting force to the portion of the spine 30 over the shoulder, the chest spine portion 31 and the pelvis 33.

Figure 9:
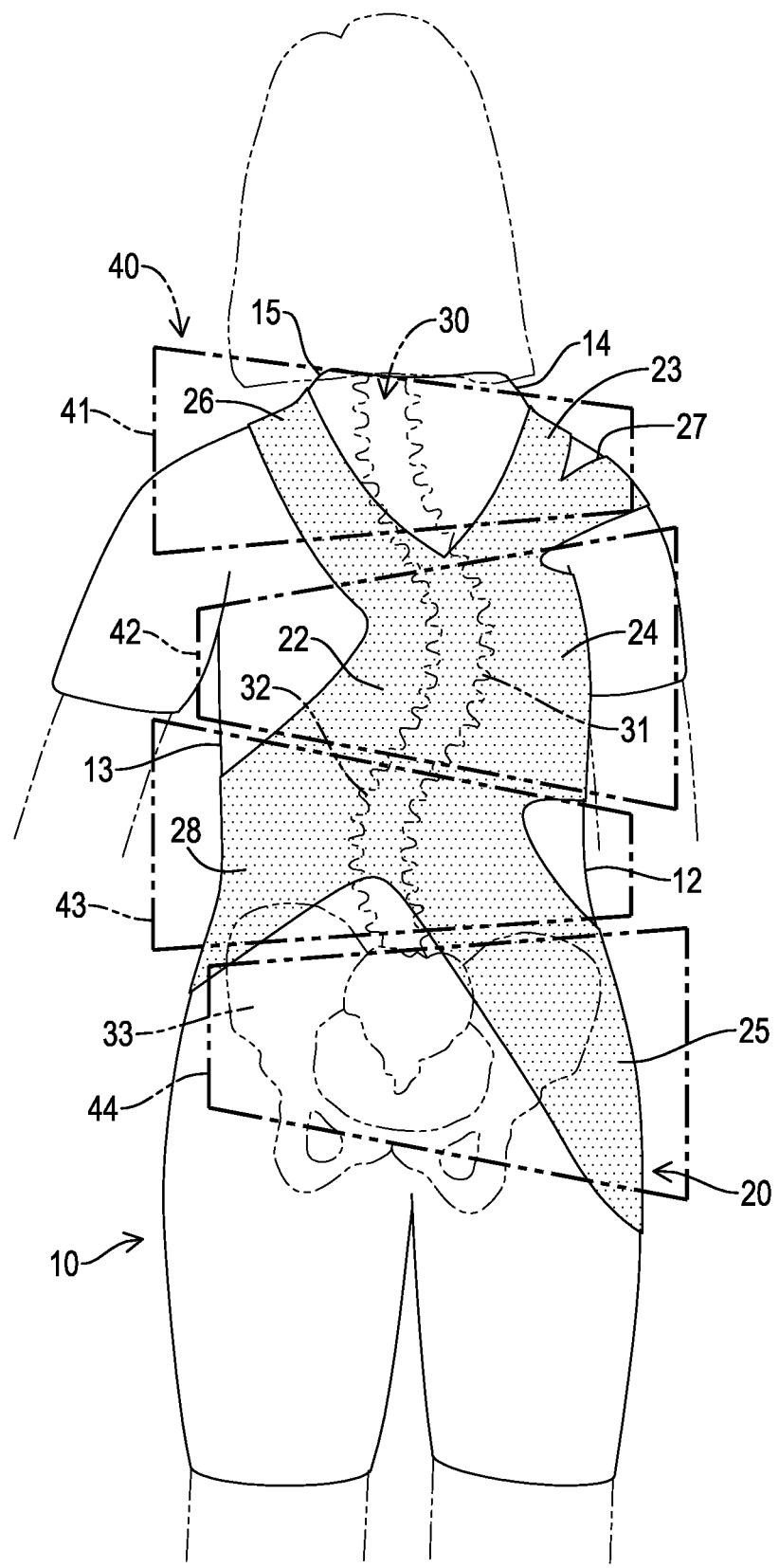
FIG. 9 is an operational schematic view of the scoliosis activity suit in FIG. 7.

With further reference to FIGS. 7 to 9, the third embodiment targets at correcting S-shaped sidebend of the spine 30, which is typically represented by the chest spine portion 31 bent toward the first side edge 12, the shoulder portion of the spine 30 over the first shoulder line 14 protracted forwards, a waist spine portion 32 bent toward the second side edge 13 and the pelvis 33 inclined toward the first side edge 12. When a user intends to wear the scoliosis activity suit, the zipper 11 on the front side of the body-wrapping portion 10 is unzipped for the scoliosis activity suit to be worn on the user. The shoulder-pulling segment 23 of the correction portion 20 provides a backward pulling force to the shoulder protracted forwards. The chest-pressing segment 24 provides a pulling force toward the second side edge 13 to the chest spine portion 31 bent toward the first side edge 12. The waist-pressing segment 28 provides a pulling force toward the first side edge 12 to the waist spine portion 32 bent toward the second side edge 13. The pelvis-lifting segment 25 provides an uplifting force to the pelvis 33 inclined toward the first side edge 12. The upper trapezius pressing segment 26 provides a supporting force to the portion of the spine 30 over the shoulder, the chest spine portion 31, the waist spine portion 32 and the pelvis 33.

Figure 12:
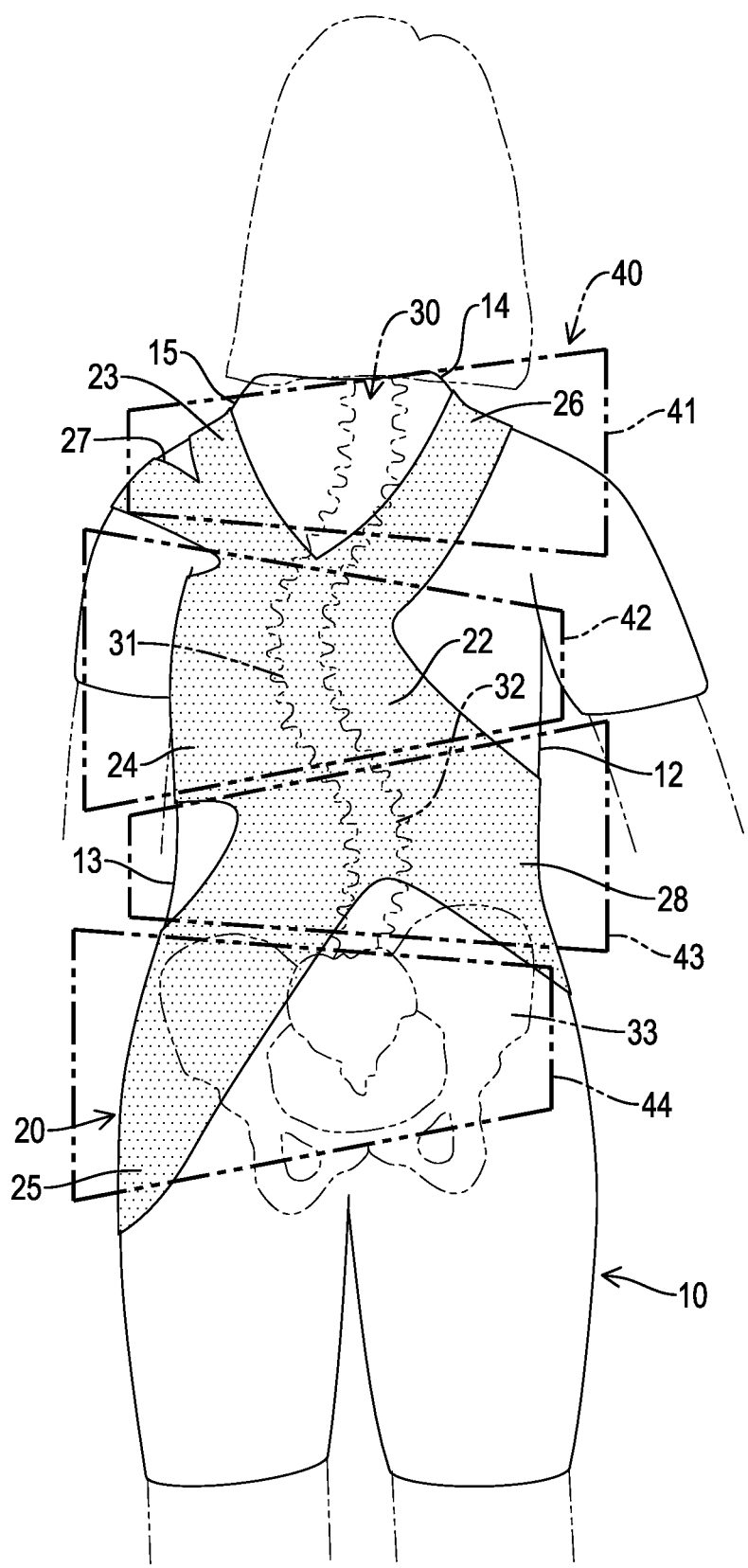
FIG. 12 is an operational schematic view of the scoliosis activity suit in FIG. 10.

With further reference to FIGS. 10 to 12, the fourth embodiment targets at correcting S-shaped sidebend of the spine 30, which is typically represented by the chest spine portion 31 bent toward the second side edge 13, the shoulder portion of the spine 30 over the second shoulder line 15 protracted forwards, a waist spine portion 32 bent toward the first side edge 12 and the pelvis 33 inclined toward the second side edge 13. When a user intends to wear the scoliosis activity suit, the zipper 11 on the front side of the body-wrapping portion 10 is unzipped for the scoliosis activity suit to be worn on the user. The shoulder-pulling segment 23 of the correction portion 20 provides a backward pulling force to the shoulder protracted forwards. The chest-pressing segment 24 provides a pulling force toward the first side edge 12 to the chest spine portion 31 bent toward the second side edge 13. The waist-pressing segment 28 provides a pulling force toward the second side edge 13 to the waist spine portion 32 bent toward the first side edge 12. The pelvis-lifting segment 25 provides an uplifting force to the pelvis 33 inclined toward the second side edge 13. The upper trapezius pressing segment 26 provides a supporting force to the portion of the spine 30 over the shoulder, the chest spine portion 31, the waist spine portion 32 and the pelvis 33.

In sum, the scoliosis activity suit in accordance with the present invention utilizes the correction portion 20 to provide a pressure to allow correction forces exerted on the shoulder-pulling segment 23, the chest-pressing segment 24, the pelvis-lifting segment 25 and the waist-pressing segment 28 based on demands of different portions of the body. The correction forces entail a backward shoulder-pulling force subjected to the protracted shoulder portion by the shoulder-pulling segment 23, an uplifting force subjected to the inclined portion of the pelvis 33 by the pelvis-lifting segment 25, a chest-pulling force subjected to the chest spine portion 31 bent toward a lateral direction opposite to the direction of the chest-pulling force by the chest-pressing segment 24, and a waist-pulling force subjected to the waist spine portion 32 bent toward a lateral direction opposite to the direction of the waist-pulling force. By virtue of the use of the zipper 11, the scoliosis activity suit can be conveniently put on and taken off to fulfill the practice of daily life adjustment and correction for scoliosis.

Even though numerous characteristics and advantages of the present invention have been set forth in the foregoing description, together with details of the structure and function of the invention, the disclosure is illustrative only. Changes may be made in detail, especially in matters of shape, size, and arrangement of parts within the principles of the invention to the full extent indicated by the broad general meaning of the terms in which the appended claims are expressed.

What is claimed is:

1. A scoliosis activity suit comprising:
 a body-wrapping portion made of elastic fabric; and
 a correction portion made of elastic fabric, formed on the body-wrapping portion, and having:
  a front segment formed on a front side of the body-wrapping portion;
  a rear segment formed on a rear side of the body-wrapping portion;

a shoulder-pulling segment formed on the front side of the body-wrapping portion, extending to the rear segment, and disconnected from the front segment;

a chest-pressing segment formed on the front side of the body-wrapping portion, connected with the front segment, and extending laterally from the front segment to the rear segment;

a pelvis-lifting segment formed on the front side of the body-wrapping portion, connected with the front segment, and extending laterally from the front segment to the rear segment;

an upper trapezius pressing segment formed on the front side of the body-wrapping portion, connected with the front segment, and extending from the front segment to the rear segment, wherein the chest-pressing segment is located between the shoulder-pulling segment and the pelvis-lifting segment; and wherein the shoulder-pulling segment has a stretchable opening formed through the shoulder-pulling segment.

2. The scoliosis activity suit as claimed in claim 1, wherein the body-wrapping portion has:

a zipper mounted on the front side of the body-wrapping portion;

a first side edge formed on a first lateral edge of the body-wrapping portion;

a second side edge formed on a second lateral edge of the body-wrapping portion and being opposite to the first side edge;

a first shoulder line formed on the body-wrapping portion and located above the first side edge; and a second shoulder line formed on the body-wrapping portion, located above the second side edge, and spaced apart from the first shoulder line.

3. The scoliosis activity suit as claimed in claim 2, wherein the shoulder-pulling segment of the correction portion extends from the front side of the body-wrapping portion to the rear segment of the correction portion through the first shoulder line, the chest-pressing segment of the correction portion extends laterally from the front segment of the correction portion to the rear segment of the correction portion through the first side edge, the pelvis-lifting segment extends laterally from the front segment of the correction portion to the rear segment of the correction portion through the second side edge, and the upper trapezius pressing segment extends from the front segment of the correction portion to the rear segment of the correction portion through the second shoulder line.

4. The scoliosis activity suit as claimed in claim 2, wherein the shoulder-pulling segment of the correction portion extends from the front side of the body-wrapping portion to the rear segment of the correction portion through the second shoulder line, the chest-pressing segment of the correction portion extends laterally from the front segment of the correction portion to the rear segment of the correction portion through the second side edge, the pelvis-lifting segment extends laterally from the front segment of the correction portion to the rear segment of the correction portion through the first side edge, and the upper trapezius pressing segment extends from the front segment of the correction portion to the rear segment of the correction portion through the first shoulder line.

5. The scoliosis activity suit as claimed in claim 2, wherein the correction portion further has a waist-pressing segment formed on the front side of the body-wrapping portion, connected with the front segment of the correction portion, extending laterally from the front segment of the correction portion to the rear segment of the correction portion, and located between the chest-pressing segment and the pelvis-lifting segment.

6. The scoliosis activity suit as claimed in claim 5, wherein the shoulder-pulling segment of the correction portion extends from the front side of the body-wrapping portion to the rear segment of the correction portion through the first shoulder line, the chest-pressing segment of the correction portion extends laterally from the front segment of the correction portion to the rear segment of the correction portion through the first side edge, the waist-pressing segment of the correction portion extends laterally from the front segment of the correction portion to the rear segment of the correction portion through the second side edge, the pelvis-lifting segment extends laterally from the front segment of the correction portion to the rear segment of the correction portion through the first side edge, and the upper trapezius pressing segment extends from the front segment of the correction portion to the rear segment of the correction portion through the second shoulder line.

7. The scoliosis activity suit as claimed in claim 5, wherein the shoulder-pulling segment of the correction portion extends from the front side of the body-wrapping portion to the rear segment of the correction portion through the second shoulder line, the chest-pressing segment of the correction portion extends laterally from the front segment of the correction portion to the rear segment of the correction portion through the second side edge, the waist-pressing segment of the correction portion extends laterally from the front segment of the correction portion to the rear segment of the correction portion through the first side edge, the pelvis-lifting segment extends laterally from the front segment of the correction portion to the rear segment of the correction portion through the second side edge, and the upper trapezius pressing segment extends from the front segment of the correction portion to the rear segment of the correction portion through the first shoulder line.

* * * * *